(12) United States Patent
Ivachtchenko et al.

(10) Patent No.: US 10,683,315 B2
(45) Date of Patent: Jun. 16, 2020

(54) PRODRUG OF AN HCV NS5B POLYMERASE INHIBITOR AND METHOD OF PRODUCTION AND APPLICATION THEREOF

(71) Applicants: Alexandre Vasilievich Ivachtchenko, Hallandale, FL (US); Andrey Alexandrovich Ivashchenko, Moscow (RU); Nikolay Filippovich Savchuk, Rancho Santa Fe, CA (US); ALLA CHEM, LLC, Hallandale, FL (US); Alena Alexandrovna Ivachtchenko, Hallandale, FL (US)

(72) Inventors: Alexandre Vasilievich Ivachtchenko, Hallandale, FL (US); Oleg Dmitrievich Mitkin, Khimki (RU)

( * ) Notice: Subject to any disclaimer, the term of this patent is extended or adjusted under 35 U.S.C. 154(b) by 0 days.

(21) Appl. No.: 15/744,094

(22) PCT Filed: Apr. 7, 2017

(86) PCT No.: PCT/RU2017/000210
§ 371 (c)(1),
(2) Date: Jan. 12, 2018

(87) PCT Pub. No.: WO2018/160089
PCT Pub. Date: Sep. 7, 2018

(65) Prior Publication Data
US 2019/0382428 A1   Dec. 19, 2019

(30) Foreign Application Priority Data
Feb. 28, 2017   (RU) ................. 2017106609

(51) Int. Cl.
*A61P 31/14*   (2006.01)
*C07F 9/6558*   (2006.01)

(52) U.S. Cl.
CPC .......... *C07F 9/65586* (2013.01); *A61P 31/14* (2018.01); *C07B 2200/13* (2013.01)

(58) Field of Classification Search
CPC .................................................. C07F 9/65586
See application file for complete search history.

(56) References Cited

U.S. PATENT DOCUMENTS 8,063,103 B2   11/2011   Davidson et al.

FOREIGN PATENT DOCUMENTS

| | | |
|---|---|---|
| EA | 200201263 A1 | 6/2003 |
| WO | WO2006135932 A2 | 12/2006 |
| WO | WO2007/068934 A2 | 6/2007 |

*Primary Examiner* — Paul V Ward

(57) ABSTRACT

The present invention relates to a prodrug and application thereof for the treatment of hepatitis C virus in patients. The prodrug of general formula 1, its stereoisomer, isotopically enriched analog, or crystalline or polymorphic form,

6 Claims, No Drawings

PRODRUG OF AN HCV NS5B POLYMERASE INHIBITOR AND METHOD OF PRODUCTION AND APPLICATION THEREOF

FIELD OF THE INVENTION

The present invention relates to chemotherapeutic agents and application thereof for the treatment of viral and cancer diseases. These compounds are the prodrugs of HCV NS5B polymerase inhibitors and are intended to treat hepatitis C in mammals.

BACKGROUND OF THE INVENTION

Hepatitis C caused by HCV is one of the world's most widely spread liver diseases. According to the annual reports of the World Health Organization (WHO), more than 130-150 mln people are infected with HCV and more than 700 thousand individuals die from HCV [WHO. Hepatitis C. WHO fact sheet No 164. Updated July 2016, http://www.who.int/mediacentre/factsheets/fs164/en/]. HCV demonstrates a high genetic diversity and is characterized by regional variations of (gT) HCV genotypes. Genotype 1 (gT1) is the most common in the world (83.4 mln people, or 46.2% of all HCV-infected; about one third of them are in East Asia). Genotype 3 (gT3) is the second most common genotype. Globally, 54.3 mln people (30.1%) are infected with gT3. Genotypes 2, 4, and 6 account for 22.8% of all HCV-infected people, while genotype 5 (gT5) accounts for <1%. While genotypes 1 and 3 prevail in the majority of countries regardless of their economic status, the greatest occurrence of genotypes 4 and 5 are in low-income states [Messina, J. P. at al. Global Distribution and Prevalence of Hepatitis C Virus Genotypes. *Hepatology* 2015, 61(1), 77-87.] Hepatitis C caused by HCV is one of the world's most widely spread liver diseases. According to the annual reports of the World Health Organization (WHO), more than 130-150 mln people are infected with HCV and more than 700 thousand individuals die from HCV [WHO. Hepatitis C. WHO fact sheet No 164. Updated July 2016, http://www.who.int/mediacentre/factsheets/fs164/en/]. HCV demonstrates a high genetic diversity and is characterized by regional variations of (gT) HCV genotypes. Genotype 1 (gT1) is the most common in the world (83.4 mln people, or 46.2% of all HCV-infected; about one third of them are in East Asia). Genotype 3 (gT3) is the second most common genotype. Globally, 54.3 mln people (30.1%) are infected with gT3. Genotypes 2, 4, and 6 account for 22.8% of all HCV-infected people, while genotype 5 (gT5) accounts for <1%. While genotypes 1 and 3 prevail in the majority of countries regardless of their economic status, the greatest occurrence of genotypes 4 and 5 are in low-income states [Messina, J. P. at al. Global Distribution and Prevalence of Hepatitis C Virus Genotypes. *Hepatology* 2015, 61(1), 77-87.].

Considerable progress in the therapy of hepatitis C that has been achieved in recent years is primarily associated with the discovery of Sofosbuvir (Sovaldi®, PSI-7977, GS-7977), which is a nucleoside prodrug of an HCV NS5B inhibitor and an Sp isomer of prodrug PSI-7851 [Sofia, M. J. et al. Discovery of a β-D-20-Deoxy-20-rfluoro-2 0-β-C-methyluridine Sovaldi Nucleotide Prodrug (PSI-7977) for the Treatment of Hepatitis C Virus. J. Med. Chem. 2010, 53, 7202-7218. Sofia, M. J. et al. Nucleoside phosphoramidate prodrugs. U.S. Pat. No. 7,964,580 (2011), U.S. Pat. No. 8,334,270 (2012). Patent RU 2478104 (2013)],

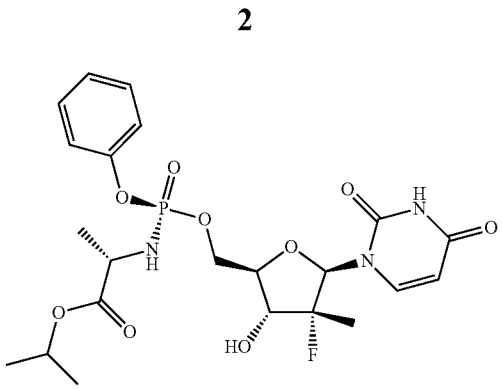

Sovaldi® (PSI-7977)

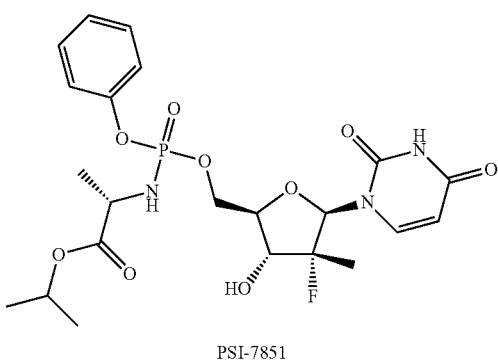

PSI-7851

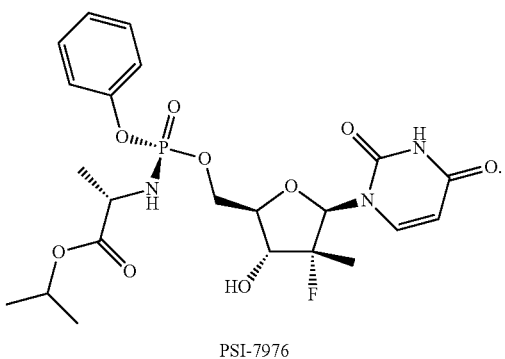

PSI-7976

Sovaldi® is now widely applied in the combination therapy of hepatitis C, including together with HCV NS5A inhibitors. Sovaldi® has become the first nucleotide approved by FDA and EC regulating agencies for the combination therapy of patients with hepatitis C infected with various HCV genotypes (gT). In clinical studies, it has shown high potency against six HCV genotypes (gT1-gT6) [I. M. Jacobson et al. Sofosbuvir for hepatitis C genotype 2 or 3 in patients without treatment options. *Engl. J. Med.* 2013, 368, 1867-1877. E. Lewirz et al. Sofosbuvir for previously untreated chronic hepatitis C infection. *Engl. J. Med.* 2013, 368, 1878-1887].

PSI-7851 and its stereoisomers PSI-7976 and PSI-7977 metabolize into triphosphate PSI-7409, which actually is an HCV NS5B polymerase inhibitor [E. Murakami et al. Mechanism of activation of PSI-7851 and its diastereoisomer PSI-7977. *J. Biol. Chem.* 2010, 285(45), 34337-34347],

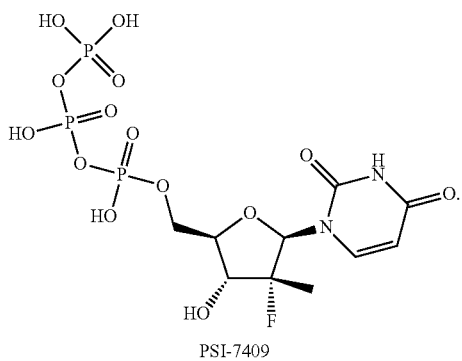 [SMILES: C[C@@]1(F)[C@H](O)[C@@H](COP(=O)(O)OP(=O)(O)OP(=O)(O)O)O[C@H]1n1ccc(=O)[nH]c1=O]

PSI-7409

There are other known Sovaldi® analogs [U.S. Pat. No. 8,334,270 (2012). M. J. Sofia et al. Discovery of a β-D-20-Deoxy-20-r-fluoro-20-β-C-methyluridine Nucleotide Prodrug (PSI-7977) for the Treatment of Hepatitis C Virus. *J. Med. Chem.* 2010, 53, 7202-7218.] including cyclohexyl (S)-2-{[(2R,3R,4R,5R)-5-(2,4-dioxo-3,4-dihydro-2H-pyrimidin-1-yl)-4-fluoro-3-hydroxy-4-methyl-tetrahydrofuran-2-ylmethoxy]-phenoxy-phosphorylamino}-propionate of formula A1, just like PSI-7851 and its phosphor stereoisomers PSI-7976 and PSI-7977 (Sovaldi®), metabolize into triphosphate PSI-7409,

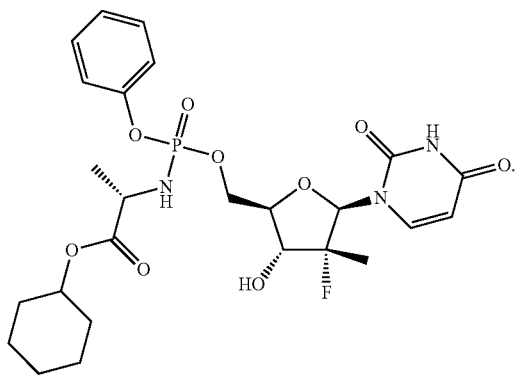

A1

However, despite recent progress in the therapy of hepatitis C, a quest for novel prodrugs of an HCV NS5B inhibitor with improved characteristics remains a major challenge.

SUMMARY OF THE INVENTION

The inventors have surprisingly found that a previously unknown compound of general formula 1 and its phosphorus stereoisomers of formulas 1.1 (Sp stereoisomer) or 1.2 (Rp stereoisomer) are potent prodrugs of an HCV NS5B polymerase inhibitor and promising antiviral agents to be used, inter alia, for the treatment of hepatitis C,

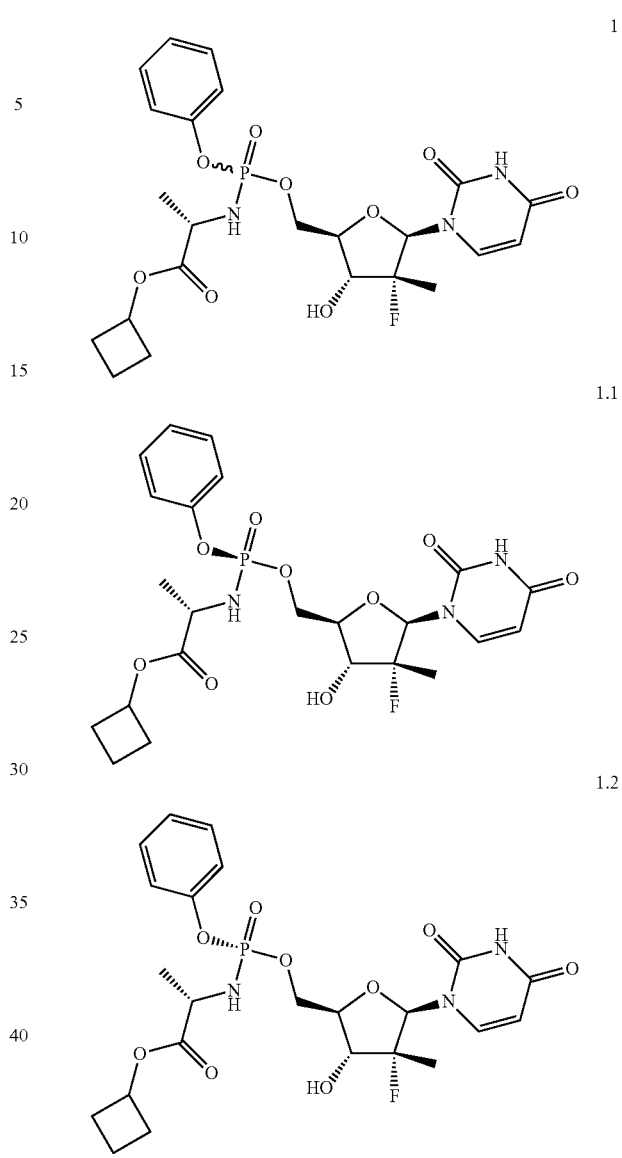

Listed below are definitions of various terms used to describe this invention. These definitions apply to the terms as they are used throughout this specification and claims, unless otherwise limited in specific instances, either individually or as part of a larger group.

The term "crystalline form" refers to a substance structure wherein the molecules are arranged to form a crystal lattice.

The term "polycrystalline form" refers to a polycrystalline substance structure consisting of a plurality of small monocrystals, or crystallites of certain crystalline form.

The term "active component" (drug substance) refers to a physiologically active compound of synthetic or other (biotechnological, plant, animal, bacterial, and so on) origins, which exhibits pharmacological activity and is an active ingredient of a pharmaceutical composition.

The term "medicinal drug" refers to a compound (or a mixture of compounds forming a pharmaceutical composition) in the form of tablets, capsules, injections, ointments, or other finished dosage forms intended for the restoration, improvement, or modification of physiological functions in humans and animals, and for the treatment and prophylaxis of diseases, for diagnostics, anesthesia, contraception, cosmetology, etc.

The term "therapeutic cocktail" refers to a simultaneously administered combination of two or more medicinal drugs that exhibit different mechanisms of pharmacological action and are directed at various biotargets taking part in the pathogenesis of disease.

The term "pharmaceutical composition" refers to a composition comprising the compound of formula 1 and at least one of the components selected from the group consisting of pharmaceutically acceptable and pharmacologically compatible fillers, solvents, diluents, carriers, auxiliary, distributing, and receptive agents, excipients, delivery agents such as preservatives, stabilizers, fillers, disintegrators, moisteners, emulsifiers, suspending agents, thickeners, sweeteners, flavoring agents, aromatizing agents, antibacterial agents, fungicides, lubricants, and prolonged delivery controllers, the choice and proportions of which depend on the nature and route of administration and dosage. Examples of suitable suspending agents are ethoxylated isostearyl alcohol, polyoxyethylene, sorbitol and sorbitol ether, microcrystalline cellulose, aluminum metahydroxide, bentonite, agar-agar and tragacant, and mixtures thereof. Protection against microorganisms can be provided using various antibacterial and antifungal agents, such as parabens, chlorobutanol, sorbic acid, and the like. Said composition may also include isotonic agents, such as sugar, sodium chloride, and the like. The sustained action of the composition can be achieved using agents that decelerate the absorption of the active ingredient, for example, aluminum monostearate and gelatin. Examples of suitable carriers, solvents, diluents and delivery agents include water, ethanol, polyalcohols and mixtures thereof, natural oils (such as olive oil), and organic esters (such as ethyl oleate) for injections. Examples of fillers are lactose, milk sugar, sodium citrate, calcium carbonate, calcium phosphate, and the like. Examples of disintegrators and distributors are starch, alginic acid and salts thereof, and silicates. Examples of lubricants are magnesium stearate, sodium lauryl sulfate, talc, and polyethylene glycol of high molecular weight. A pharmaceutical composition for peroral, sublingval, transdermal, intramuscular, intravenous, subcutaneous, and local or rectal administration of the active ingredient, alone or in combination with another active compound, may be administered to animals and people in a standard administration form as a mixture with traditional pharmaceutical carriers. Suitable standard administration forms include peroral forms, such as tablets, gelatin capsules, pills, powders, granules, chewing gums, and peroral solutions or suspensions; sublingval and transbuccal administration forms; aerosols; implants; local, transdermal, subcutaneous, intramuscular, intravenous, intranasal, or intraocular forms; and rectal administration forms.

The term "inert filler" as used herein refers to a compound that is used for forming a pharmaceutical composition and is, as a rule, safe, nontoxic, and neither biologically nor otherwise undesirable, and comprises excipients acceptable for veterinary and human pharmaceutical use. Compounds of this invention may be administered individually but are generally administered in a mixture with one or more pharmaceutically acceptable excipients, diluents, or carriers chosen depending on the contemplated route of drug administration and standard pharmaceutical practice.

The term "therapeutically effective amount," as used herein, refers to an amount of a substance, prodrug, or drug needed for alleviating the symptoms of the disease in the subject. The dose of a substance, prodrug, or drug will meet individual demands in each particular case. Said dose may vary in a wide range depending on numerous factors like the severity of the disease to be treated, the age and the general condition of the patient, other medicaments used for the patient's treatment, the mode and route of administration, and the experience of the attending doctor. For oral administration, the daily dose is approximately 0.01-10 g, including all values therebetween, both in monotherapy and/or combination therapy. The preferred daily dose is around 0.1-7 g. As a rule, in order to alleviate or eliminate the virus, a higher loading dose is given at the beginning of treatment with a subsequent reduction of the dose to a level sufficient to prevent an infection burst.

The term "subject" refers to a mammal including, but not limited to, cattle, hogs, sheep, chickens, turkeys, buffalos, lamas, ostriches, dogs, cats, and humans; a human subject is most preferable. It is assumed that a subject's treatment may involve the use of the prodrug of general formula 1, its stereomer, isotopically enriched analog, pharmaceutically acceptable salt, hydrate, solvate, and crystalline or polymorphic form or their combinations with another compound, including with an HCV NS5A inhibitor.

The subject matter of the present invention is cyclobutyl (S)-2-{[(2R,3R,4R,5R)-5-(2,4-dioxo-3,4-dihydro-2H-pyrimidin-1-yl)-4-fluoro-3-hydroxy-4-methyl-tetrahydrofuran-2-ylmethoxy]-phenoxy-phosphorylamino}-propanoate of general formula 1, its phosphorus stereoisomers (Sp stereoisomer of formula 1.1 or Rp stereoisomer of formula 1.2), their isotopically enriched analog, or crystalline or polycrystalline forms.

The subject matter of the present invention is a prodrug of an HCV NS5B polymerase inhibitor of general formula 1, its phosphorus stereoisomer (Sp stereoisomer of formula 1.1 or Rp stereoisomer of formula 1.2), their isotopically enriched analog, or crystalline or polycrystalline forms as a medicinal drug for the treatment of hepatitis C in humans or warm-blooded animals in need thereof in need thereof.

Preferable prodrugs are cyclobutyl (S)-2-{(S)-[(2R,3R,4R,5R)-5-(3,4-dihydro-2,4-dioxo-2H-pyrimidin-1-yl)-3-hydroxy-4-methyl-4-fluoro-tetrahydrofuran-2-ylmethoxy]-phenoxy-phosphorylamino}-propanoate (1.1), its isotopically enriched analog, or crystalline or polycrystalline form.

Surprisingly, the novel prodrug of general formula 1, its phosphorus stereoisomers, their isotopically enriched analogs, and crystalline and polycrystalline forms appeared to be a more effective prodrug of an HCV NS5B inhibitor than known prodrugs of HCV NS5B inhibitors and, in particular, more potent than Sovaldi® and cyclohexyl ester of formula A1.

Indeed, Sovaldi® has against HCV genotype 1b (gT1b) $EC_{50}$=0.045-0.170 µM [http://www.hcvdruginfo.ca/downloads/HCV_Sofosbuvir.pdf] and $EC_{90}$=0.59 µM, while the novel prodrug of formula 1.1 has $EC_{50}$=15.0-27.0 nM and $EC_{90}$=128.0 nM (Table 1a), which means that the novel prodrug of formula 1.1 is more than three times more active than Sovaldi®. The half-life of the prodrug of formula 1.1 in human liver microsomal S9 fraction is $T_{1/2}^{hS9}$=0.05 h, while Sovaldi® has $T_{1/2}^{hS9}$=0.54 h (Table 2), which means that the metabolic rate of the novel prodrug of formula 1.1 in human liver microsomal S9 fraction is 11 times faster than that of Sovaldi®. In addition, the concentration and $AUC_{24h}$ of triphosphate PSI-7409 in the rat liver resulting from the metabolic process of the prodrug of formula 1.1 are $C_{max}$=3 224.0 ng/g and $AUC_{24h}$=30 487.0 ng·h/g, respectively, while Sovaldi's similar metabolism leads to $C_{max}$=1 934.0 ng/g and $AUC_{24h}$=16 796.0 ng·h/g (Table 3). This testifies to the fact that the novel prodrug of formula 1.1 metabolizes into requisite triphosphate PSI-7409 (drug) in the liver almost two times more effectively.

The novel prodrug of formula 1.1 has even greater efficiency in comparison with known cyclohexyl ester of formula A1, because said prodrug is known [M. J. Sofia et al. J. Med. Chem. 2010, 53, 7202-7218] to have the following parameters: $EC_{90}=250.0$ nM, $T_{1/2}^{hS9}=1.4$ h, $C_{max}=557$ ng/g and $AUC_{24h}=6\,484.0$ ng·h/g.

The results (effect) obtained are surprising, because the prodrug of formula 1.1, which is cyclobutyl ester, is not just much more effective than its analog—cyclohexyl ester of formula A1, but more active than another analog—cyclopropyl ester of formula A2 ($EC_{90}=73.0$ nM, $EC_{90}=410.0$ nM, see Table 1a), which was specially prepared by the inventors to better illustrate said surprising effect,

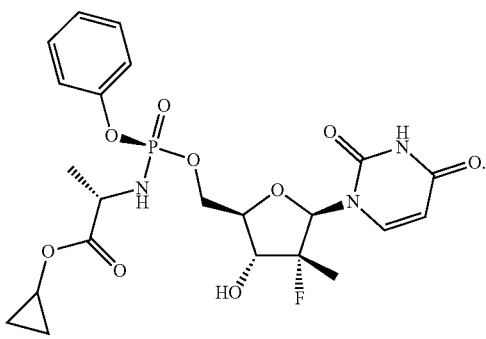

A2

The surprise is that in the series of cycloalkyl esters, the most effective one appeared to be cyclobutyl ester of formula 1.1 with a medium-sized cycloalkyl, while esters with a larger-size cycloalkyl (known cyclohexyl ester of formula A1) and a smaller-size cycloalkyl (cyclopropyl ester of formula A.2 specially prepared by the inventors) appeared to be less effective.

The above data are a convincing proof of the novelty and the level (effectiveness) of this invention.

The subject matter of the present invention is a medicinal drug possessing the properties of an HCV NS5B polymerase inhibitor, said medicinal drug being the compound of general formula 1, its stereoisomer, isotopically enriched analog, or crystalline or polycrystalline form in a therapeutically effective amount intended for the treatment of hepatitis C in humans or warm-blooded animals in need thereof.

The subject matter of the present invention is a pharmaceutical composition in a therapeutically effective amount comprising the prodrug of general formula 1, its stereoisomer, isotopically enriched analog, crystalline or polycrystalline form, optionally in combination with a pharmaceutically acceptable filler, carrier, additive, or diluent for the treatment of hepatitis C virus in mammals.

Said prodrug of general formula 1, its stereoisomer, isotopically enriched analog, crystalline or polycrystalline forms may be prepared in a variety of peroral dosage forms and carriers; peroral administration may be effected in the form of tablets, film-coated tablets, hard and soft gelatin capsules, solutions, emulsions, syrups, or suspensions. The compounds of this invention are effective when administered in the form of suppositories. Generally, the most convenient route of administration is peroral using a common daily dosage regimen that can be adjusted depending on the severity of disease and a patient's antiviral or antitumor drug reaction.

The prodrug of general formula 1, its stereoisomer, isotopically enriched analog or crystalline or polycrystalline form in combination with one or more common excipients, carriers, or diluents may be in the form of pharmaceutical compositions and unit dosage forms thereof. Pharmaceutical compositions and standard dosage forms may consist of ordinary ingredients in usual proportions with or without additional active compounds and dosage forms. The pharmaceutical composition may comprise any appropriate effective amount of active ingredient depending on the prescribed daily dose. Pharmaceutical compositions may be used in the form of solid substances, such as tablets or filled capsules; in the form of semisolid powders, agents with sustained release or liquids such as suspensions, emulsions, or filled capsules for peroral administration; or in the form of suppositories for rectal or vaginal administration. A typical medication will comprise approximately from 5 wt % to 95 wt % of the active compound or a compound. The terms "medication" or "dosage form" are meant to include both solid and liquid compositions of active compound, so that it would be clear for a person skilled in the art that the active ingredient may exist in the form of different medications depending on the dose required and pharmacokinetic parameters.

Solid dosage forms include powders, tablets, pills, capsules, suppositories, and dispersible granules. A solid carrier refers to one or more substances that can act as diluents, flavors, solubilizers, lubricants, suspending agents, binding agents, preservatives, disintegrants, or encapsulating material. A powder carrier is generally a fine-grained solid mixed with a fine-grained active component. In the tablets, the active component is usually mixed, in appropriate proportions, with a carrier having a necessary binding capacity and compacted into the desired shape and size. Suitable carriers include, but are not limited to, magnesium carbonate, magnesium stearate, talc, sugar, lactose, pectin, dextrin, starch, gelatin, tragacant, methylcellulose, sodium carboxymethylcellulose, low-melting wax, cocoa butter, and the like. Solid preparations may, in addition to the active ingredient, comprise dyes, flavoring agents, stabilizers, buffers, artificial and natural sweeteners, dispersants, thickeners, solubilizers, and the like.

Liquid compositions are suitable for peroral administration too. Liquid dosage forms include emulsions, syrups, elixirs, and aqueous suspensions. They comprise solid drug forms to be converted to liquid medications immediately before use. Emulsions may be prepared in solutions, for example, in aqueous solutions of propylene glycol, or they may comprise emulsifiers, such as lecithin, sorbitol monooleate, or gum arabic. Aqueous suspensions may be prepared by dispersing a fine-grained active ingredient in water with ductile materials, such as natural or synthetic gums, resins, methylcellulose, sodium carboxymethylcellulose, and other well-known suspending agents.

The prodrug of general formula 1, its stereoisomer, isotopically enriched analog, crystalline or polycrystalline form may be prepared for administration in the form of suppositories. Low-melting wax, such as a mixture of glycerides of fatty acids or cocoa butter, is first melt and then the active ingredient is homogeneously dispersed by, for example, stirring. The molten homogeneous mixture is poured into moulds of a suitable size and allowed to cool and solidify.

The prodrug of general formula 1, its stereoisomer, isotopically enriched analog, crystalline or polycrystalline form may be prepared for vaginal administration. It will be appropriate to apply suppositories, tampons, creams, gels, pastes, foams, or sprays comprising, in addition to the active ingredient, carriers that are well known in the art.

The subject matter of the present invention is the application of the prodrug of general formula 1, its stereoisomer, isotopically enriched analog, crystalline or polycrystalline form in the production of a medicinal drug for the treatment of hepatitis C virus. It is assumed that the prodrug of general formula 1, its stereoisomer, isotopically enriched analog, crystalline or polycrystalline form used in the production of said medicinal drug for the treatment of any viral disease described herein may be any of the compounds of general formula 1 selected from cyclobutyl (S)-2-{[(2R,3R,4R,5R)-5-(3,4-dihydro-2,4-dioxo-2H-pyrimidin-1-yl)-3-hydroxy-4-methyl-4-fluoro-tetrahydrofuran-2-ylmethoxy]-phenoxy-phosphorylamino}-propanoate (1), cyclobutyl (S)-2-{(S)-[(2R,3R,4R,5R)-5-(3,4-dihydro-2,4-dioxo-2H-pyrimidin-1-yl)-3-hydroxy-4-methyl-4-fluoro-tetrahydrofuran-2-ylmethoxy]-phenoxy-phosphorylamino}-propanoate (1.1), and cyclobutyl (S)-2-{(R)-[(2R,3R,4R,5R)-5-(3,4-dihydro-2,4-dioxo-2H-pyrimidin-1-yl)-3-hydroxy-4-methyl-4-fluoro-tetrahydrofuran-2-ylmethoxy]-phenoxy-phosphorylamino}-propanoate (1.2), their isotopically enriched analog or crystalline or polycrystalline form either individually or in combination with some other compound of this invention.

The subject matter of the present invention is a method for the combination treatment and/or prophylaxis of viral and cancer diseases in a subject in need thereof, said method involving administration to the subject of a therapeutically effective amount of the prodrug of general formula 1, its stereoisomer, isotopically enriched analog, or crystalline or polycrystalline form and a therapeutically effective amount of some other antiviral or anticancer agent, wherein agents are administered simultaneously or alternatively. It is understood that there may be any time span, ranging from 1 to 24 h, between the successive administrations of agents.

Examples of "other antiviral agents" include, but are not limited to, HCV NS3 protease inhibitors [US 20140296136, U.S. Pat. Nos. 8,987,195, 7,973,040, US 2012214783], HCV NS4 inhibitors [EP1497282], HCV NS3NS4 inhibitors [EP 2364984], and HCV NS5A inhibitors [C. Wang et al. Hepatitis C virus RNA elimination and development of resistance in replicon cells treated with BMS-790052. Antimicrob. Agents Chemother. 2012, -5658. 1350 https://en-.wikipedia.org/wiki/Daclatasvir; A. V. Ivachtchenko et al. Discovery of Novel Highly Potent Hepatitis C Virus NS5A Inhibitor (AV4025). J. Med. Chem. 2014, 57, 77167730; U.S. patent application Ser. No. 14/845,333); Toll-like receptor agonists (WO 2015023958, WO 2012097012); and other inhibitors (WO 2014106019, WO 2014033176, WO 2014033170, WO 2014033167, WO 2013006394, US 20090163545].

More preferable is an antiviral pharmaceutical composition, which, along with the novel prodrug of general formula 1 or its stereoisomer of formula 1.1, isotopically enriched analog, crystalline or polycrystalline form, additionally comprises an antiviral or anticancer medicinal drug in a therapeutically effective amount.

More preferable is an antiviral pharmaceutical composition, which, along with the novel prodrug of general formula 1 or its stereoisomer of formula 1.1, isotopically enriched analog, crystalline or polycrystalline form, additionally comprises a therapeutically effective amount of an HCV NS5A inhibitor selected from the group including:

Daclatasvir (Daklinza, BMS790052) [Belema, M. et al. Discovery and Development of Hepatitis C Virus NS5A Replication Complex Inhibitors. J. Med. Chem. 2014, 57, 1643-1672. Bachand, C. et al. Hepatitis C virus inhibitors. Patent WO 2008/021927, 2008. Bachand, C. et al. Hepatitis c virus inhibitors. Patent WO 2008/021928, 2008. Bachand, C. et al. Hepatitis C virus inhibitors. Patent WO 2008/021936, 2008. http://www.ema.europa.eu/docs/en_GB/document_library/EPAR_Public_assessment report/human/003768/WC500172849.pdf.]

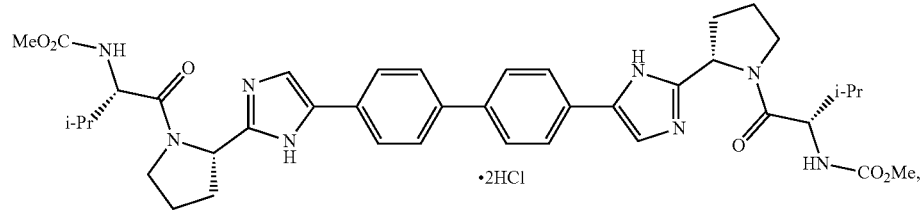

Declatasvir (BMS-790052)

Hepavivir (AV-4025) [Ivachtchenko, A. V. et al. Discovery of Novel Highly Potent Hepatitis C Virus NS5A Inhibitor (AV4025). J. Med. Chem. 2014, 57, 7716-7730. Patent WO 2012/074437, 2012. U.S. Pat. No. 9,428,491, 2016.]

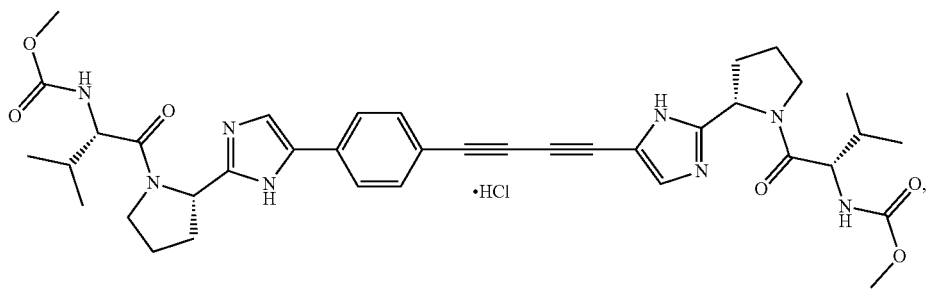
Hepavivir (AV-4025)
AV-4056 and AV-4058 [U.S. Pat. No. 9,428,491.]
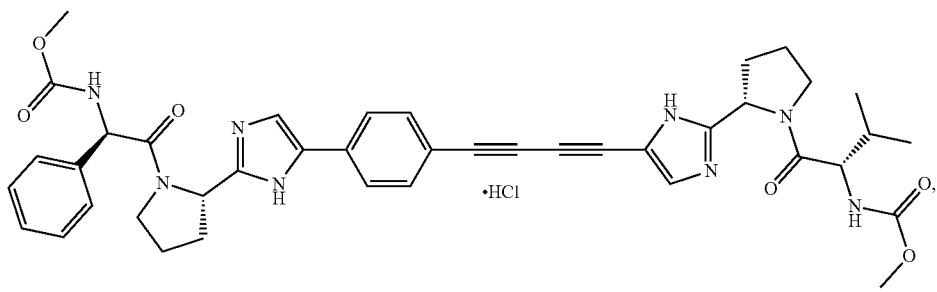
AV-4056
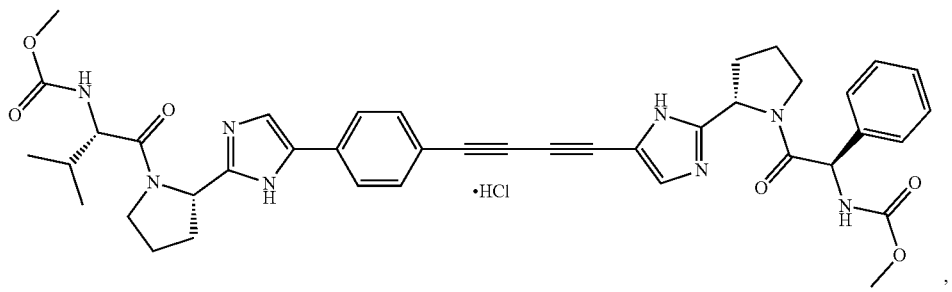
AV-4058
AV-4067 and AV-4084 [U.S. patent application Ser. No. 14/845,333.]

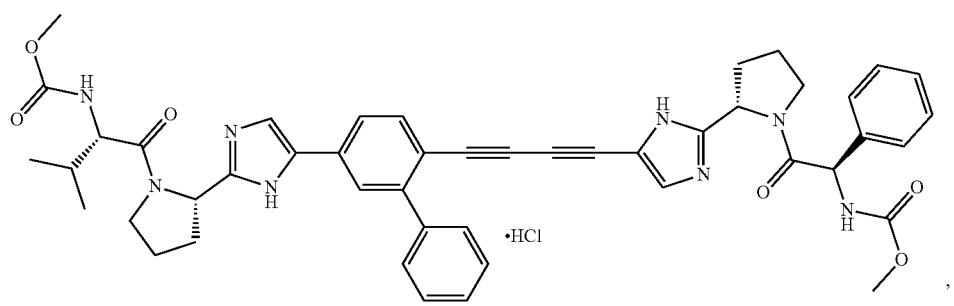
AV-4067
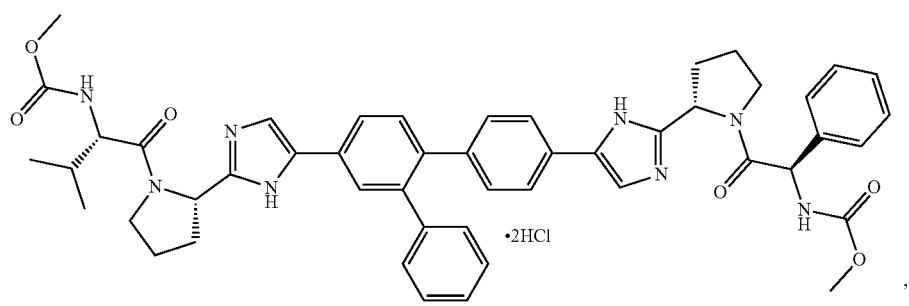
AV-4084
Ombitasvir (ABT-267) [Gardelli, C. et al. Phosphoramidate Prodrugs of 20-C-Methylcytidine for Therapy of Hepatitis C Virus Infection. *J. Med. Chem.* 2014, 57, 2047-2057. Patent WO 2010/144646, 2010.]
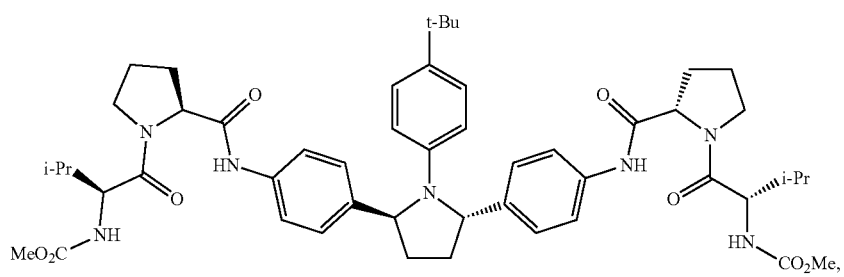
Ombitasvir (ABT-267)
Elbasvir (MK-8742), [Coburn, C. A. et al. *ChemMedChem.* 2013, 8, 1930-1940. Patent WO 2012/040923, 2012. Patent WO 2012/041014, 2012]

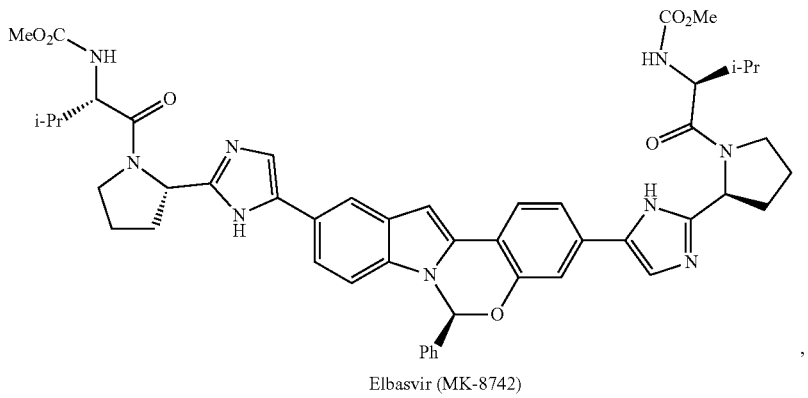 [SMILES: COC(=O)N[C@H](C(=O)N1CCC[C@H]1c1ncc(-c2ccc3c(c2)O[C@@H](c2ccccc2)n2c-3cc3cc(-c4cnc([C@@H]5CCCN5C(=O)[C@@H](NC(=O)OC)C(C)C)[nH]4)ccc32)[nH]1)C(C)C]

Elbasvir (MK-8742)

Velpatasvir (VEL, GS-5816), [Patent WO 2015/110048, 2015. http://www.accessdata.fda.gov/drugsatfdadocs/nda/ 2016/208341O rig1s000PharmR.pdf]. http://www.gilead.com/~/media/files/pdfs/medicines/liver-disease/epclusa/epclusa_pi.pdf]

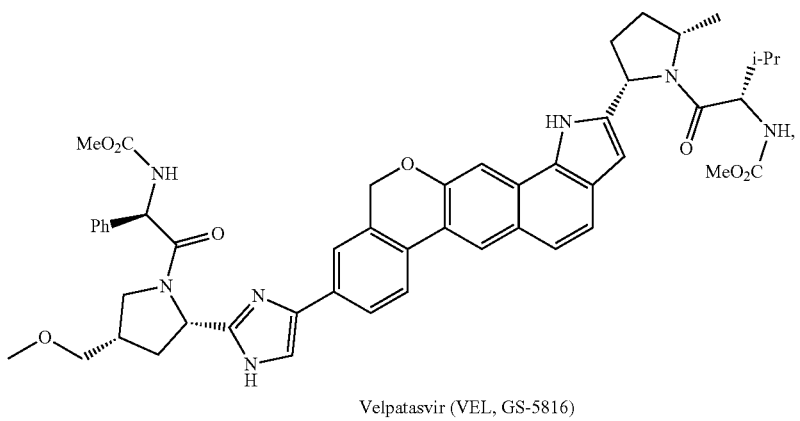 [SMILES: COC[C@H]1C[C@@H](c2nc(-c3ccc4c(c3)COc3cc5c(ccc6cc([C@@H]7CC[C@H](C)N7C(=O)[C@@H](NC(=O)OC)C(C)C)[nH]c65)cc3-4)c[nH]2)N(C(=O)[C@H](NC(=O)OC)c2ccccc2)C1]

Velpatasvir (VEL, GS-5816)

Narlaprevir (SCH 900518), an inhibitor of HCV non-structural protein 3 (NS3) [Arasappan A. et al. Discovery of Narlaprevir (SCH 900518): A Potent, Second Generation HCV NS3 Serine Protease Inhibitor. *ACS Med. Chem. Lett.*, 2010, 1 (2), 64-69]

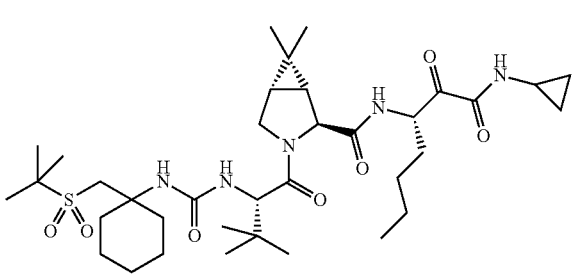

Narlaprevir (SCH 900518)

and Simeprevir (Olysio), an inhibitor of HCV non-structural protein NS3/NS4 [https://www.tga.gov.au/sites/default/files/auspar-simeprevir-141027-pi.docx]

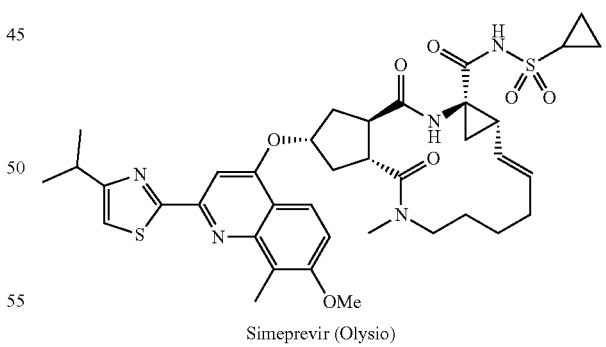

Simeprevir (Olysio)

The subject matter of the present invention is a method for the combination treatment of viral and cancer diseases in a subject in need thereof, said method involving successive or simultaneous administration of a therapeutically effective amount of the prodrug of general formula 1, its stereoisomer, isotopically enriched analog, crystalline or polycrystalline form, or some other antiviral or anticancer agent. It is understood that there may be any time span between the successive administrations of agents.

It is assumed that the other antiviral agent is, but is not limited to, interferon alpha, interferon beta, pegylated interferon alpha, ribavirin, levovirin, viramidine, another nucleoside HCV polymerase inhibitor, non-nucleoside HCV polymerase inhibitor, HCV protease inhibitor, HCV helicase inhibitor or HCV fusion inhibitor, HBV DNA polymerase inhibitor, and HIV 1 reverse transcriptase (RT) inhibitor. When the prodrug or a derivative or salt thereof is administered in combination with another antiviral or anticancer agent, the activity may be increased against the initial activity of the prodrug. In combination therapy, the administration of agents may be simultaneous or successive regarding the prodrug of general formula 1. The notion "simultaneous administration" as used herein thus means administration of agents at the same time or at different times. The administration of two or more agents at the same time may be performed by using one preparative form comprising two or more active ingredients or, in essence, by simultaneously administering two or more dosage forms with one active agent. It should be understood that any reference to therapy as used herein covers prophylaxis as well. In addition, the term "therapy" of viral infection, as used herein, includes treatment or prophylaxis of a disease or a condition associated with a mediated viral infection or clinical symptoms thereof.

The present invention relates to a method for the production of the prodrug of general formula 1 and a stereoisomer, isotopically enriched analog, and crystalline and polycrystalline forms thereof, said method involving the use of previously unknown cyclobutyl (S)-2-(pentafluorophenyloxy-phenoxy-phosphorylamino)-propionate of formula 2 or its stereoisomers cyclobutyl (S)-2-((S)-pentafluorophenyloxy-phenoxy-phosphorylamino)-propionate of formula 2.1 and cyclobutyl (S)-2-((R)-pentafluorophenyloxy-phenoxy-phosphorylamino)-propionate of formula 2.2, which are also the subject matter of the present invention,

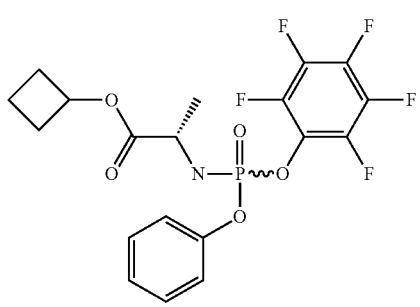

2

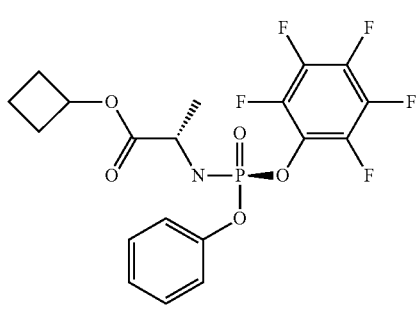

2.1

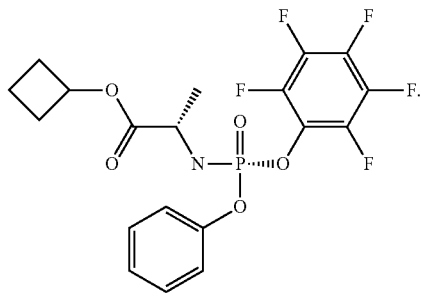

2.2

The inventors have surprisingly found that the novel prodrug of general formula 1 and its phosphorus stereoisomers (Sp-stereoisomer of formula 1.1 and Rp-stereoisomer of formula 1.2) are more effective prodrugs of HCV NS5B inhibitors than, for example, known Sovaldi® and cyclohexyl ester of formula A1 as well as previously unknown cyclopropyl ester (comparator) of formula A2.

Thus, Sovaldi® has against HCV genotype 1b (gT1b) $EC_{50}$=0.045-0.170 µM and $EC_{90}$=590 nM, cyclohexyl ester of formula A1 has $EC_{90}$=250.0 nM, while cyclopropyl ester of formula A2 has $EC_{90}$=73.0 nM and $EC_{90}$=410.0 nM (Table 1). The novel prodrug of formula 1.1 has $EC_{50}$=15.0-27.0 nM and $EC_{90}$=128.0 nM (Table 1a), which means that the novel prodrug of formula 1.1 is more than three times more active than Sovaldi®, twice as active as the compound of formula A1, and more than thrice as active as the compound of formula A2.

The half-life of the prodrug of formula 1.1 in human liver microsomal S9 fraction is $T_{1/2}^{hS9}$=0.05 h, while Sovaldi® has $T_{1/2}^{hS9}$=0.54 h and cyclohexyl ester of formula A1, $T_{1/2}^{hS9}$=1.4 h, (Table 2), which means that the metabolic rate of the novel prodrug of formula 1.1 in human liver microsomal S9 fraction is 11 times faster than that of Sovaldi® and B 28 times faster than that of cyclohexyl ester of formula A1. In addition, the concentration and $AUC_{24h}$ of triphosphate PSI-7409 in the rat liver resulting from the metabolic process of the prodrug of formula 1.1 are $C_{max}$=3 224.0 ng/g and $AUC_{24h}$=30 487.0 ng·h/g, respectively, while Sovaldi's similar metabolism leads to Cmax=1 934.0 ng/g and $AUC_{24h}$=16 796.0 ng·h/g (Table 3). This testifies to the fact that the novel prodrug of formula 1.1 metabolizes into requisite triphosphate PSI-7409 (drug) in the liver almost two times more effectively than Sovaldi® and 4.7 times more effectively than cyclohexyl ester of formula A1.

The results (effect) obtained are surprising, because the prodrug of formula 1.1, which is cyclobutyl ester, is not just much more effective than its analog—cyclohexyl ester of formula A1, but more active than another analog—cyclopropyl ester of formula A2 ($EC_{90}$=73.0 nM, $EC_{90}$=410.0 nM, see Table 1a), which was specially prepared by the inventors to better illustrate said surprising effect.

BEST EMBODIMENT

The present invention will now be described in terms of certain embodiments which are not intended to limit its scope. On the contrary, the present invention covers all alternatives, modifications, and equivalents that can be included within the scope of the claims. Thus, the following examples, which include specific embodiments, will illustrate this invention without limiting it.

Example 1. Synthetic Protocol for the Prodrug of Cyclobutyl (S)-2-{[(2R,3R,4R,5R)-5-(3,4-dihydro-2,4-dioxo-2H-pyrimidin-1-yl)-3-hydroxy-4-methyl-4-fluoro-tetrahydrofuran-2-ylmethoxy]-phenoxy-phosphorylamino}-propanoate of General Formula 1 and Stereoisomers 01.1 and 1.2 Thereof (Scheme 1)

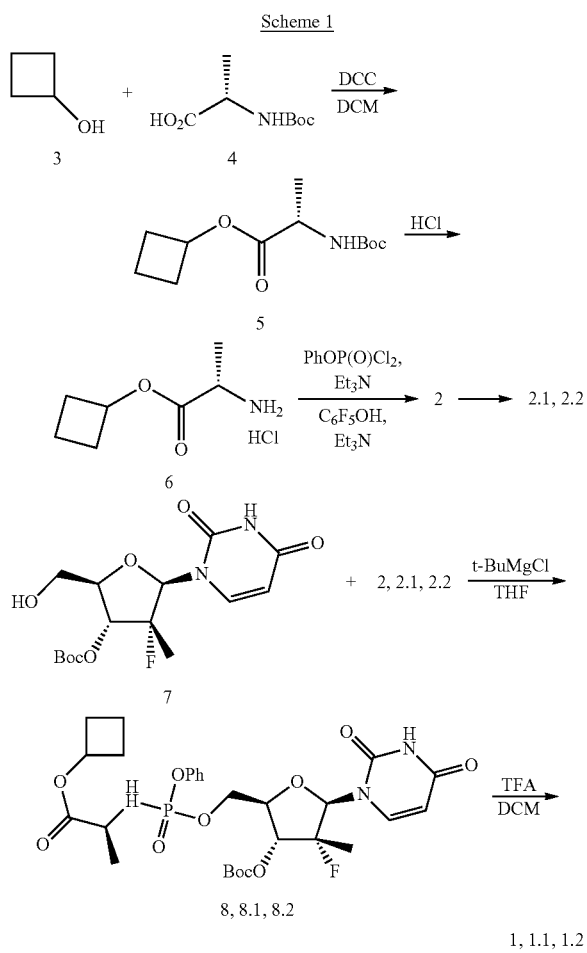

To a solution of N-Boc-L-alanine (4: 15.5 g, 81.9 mmol) in dichloromethane (300 ml), DCC (16.9 g, 81.9 mmol) was added at 0° C. and 5 min later, cyclobutanol (3: 5.6 g, 78.0 mmol) and DMAP (2.0 g, 16.4 mmol). The mixture was left to stir overnight at room temperature, evaporated in vacuum, and the residue was treated with ethyl acetate (300 ml). The residue was filtered off and washed with ethyl acetate. The filtrate was washed with a 5% solution of citric acid (2×100 ml), a saturated NaHCO₃ solution (2×100 ml), and brine, dried over Na$_2$SO$_4$, and evaporated in vacuum to afford 19.6 g (98%) of (S)-cyclobutyl 2-(tert-butoxycarbonylamino)propanoate (5) as a white powder. $^1$H NMR (400 MHz, DMSO-d$_6$) δ 7.22 (d, J=7.2 Hz, 0.85H), 6.87 (m, 0.15H), 4.89 (p, J=7.2 Hz, 1H), 3.94 (m, 1H), 2.26 (m, 2H), 1.98 (m, 2H), 1.74 (m, 1H), 1.59 (m, 1H), 1.38 (s, 7.5H), 1.34 (brs, 1.5H), 1.22 (d, J=7.2 Hz, 3H).

To a solution of compound 5 (19.6 g, 80.6 mmol) in dioxane (50 ml), HCl (230 ml, 3M) in dioxane was added, the mixture was allowed to stir overnight and evaporated in vacuum. The residue was treated with ether (400 ml) and stirred overnight. The residue was filtered off, washed with ether, and dried in vacuum to afford 14.1 g (97%) of (S)-cyclobutyl 2-amino-propanoate hydrochloride (6) as a white powder. $^1$H NMR (400 MHz, DMSO-d$_6$) δ 8.56 (brs, 3H), 5.00 (p, J=7.6 Hz, 1H), 4.02 (q, J=7.2 Hz, 1H), 2.31 (m, 2H), 2.07 (m, 2H), 1.78 (m, 1H), 1.62 (m, 1H), 1.41 (d, J=7.2 Hz, 3H).

Phenyl dichlorophosphate (16.9 g, 80.2 mmol) was added to a solution of compound 6 (14.4 g, 80.2 mmol) in dichloromethane (214 ml). The mixture was cooled to −75-70° C., and a solution of triethylamine (16.2 g, 160.4 mmol) in dichloromethane (16 ml) was added dropwise while maintaining the temperature at −75-70° C. The mixture was stirred at −70° C. for 30 min and then heated to −20° C. A solution of pentafluorophenol (14.6 g, 79.4 mmol) in dichloromethane (105 ml) was added at −20-10° C., then a solution of triethylamine (8.1 g, 80.2 mmol) in dichloromethane (8 ml) was added dropwise, and the mixture was left to stir overnight at room temperature. The mixture was evaporated in vacuum, ethyl acetate (500 ml) and water (500 ml) were added, the organic layer was separated, washed with 5% NaHCO₃ solution, brine, dried over Na$_2$SO$_4$ and evaporated in vacuum. A mixture of hexane and ethyl acetate (200 ml, 6:1) was added to the residue, and the mixture was left to stir overnight. The resulting residue was filtered off, washed with a 6:1 hexane/ethyl acetate mixture (50 ml), and air-dried to afford 16.7 g of cyclobutyl (S)-2-((perfluorophenoxy)(phenoxy)phosphorylamino)propanoate (2).

The resulting product (2) was recrystallized from a hexane/ethyl acetate (4:1) mixture (500 ml) to afford 13.8 g (37%) of cyclobutyl (S)-2-((S)-(perfluorophenoxy)-(phenoxy)-phosphorylamino)propanoate (2.1) as a white loose powder. $^1$H NMR (300 MHz, DMSO-d$_6$) δ 7.42 (m, 2H), 7.24 (m, 3H), 6.87 (dd, J, =14.1 Hz, J$_2$=10.2 Hz, 1H), 4.87 (p, J=7.5 Hz, 1H), 3.94 (m, 1H), 2.23 (m, 2H), 1.94 (m, 2H), 1.71 (m, 1H), 1.58 (m, 1H), 1.27 (d, J=7.2 Hz, 3H). The generic solution left after washing with a mixture of hexane/ethyl acetate (6:1) during recrystallization of the compound of formula 2.1 was evaporated in vacuum and thrice recrystallized from hexane to afford cyclobutyl (S)-2-((R)-(perfluorophenoxy)-(phenoxy)-phosphorylamino)propanoate (2.2) as a white loose powder. $^1$H NMR (300 MHz, DMSO-d$_6$) δ 7.42 (m, 2H), 7.26 (m, 3H), 6.85 (dd, J, =13.8 Hz, J$_2$=10.2 Hz, 1H), 4.88 (p, J=7.5 Hz, 1H), 3.95 (m, 1H), 2.24 (m, 2H), 1.93 (m, 2H), 1.72 (m, 1H), 1.59 (m, 1H), 1.28 (d, J=6.9 Hz, 3H).

To a solution of tert-butyl (2R,3R,4R,5R)-5-(2,4-dioxo-3,4-dihydropyrimidin-1(2H)-yl)-2-(hydroxymethyl)-4-methyl-4-fluoro-tetrahydrofuran-3-yl carbonate (7: 5 g, 13.9 mmol) in THF (165 ml), a 1M solution of tert-butylmagnezium chloride in THF (31.3 ml, 31.3 mmol) was added under argon at 0° C., and the mixture was stirred for 30 min at room temperature. A solution of the compound of formula 2.1 (7.8 g, 16/7 mmol) in THF (30 ml) was added at 0-5° C. using a syringe, and the mixture was stirred under argon for 24 hours. Upon addition of methanol (10 ml), the mixture was evaporated in vacuum. The residue was dissolved in 500 ml of ethyl acetate, washed with 5% solution of citric acid, 5% solution of NaHCO₃, dried over Na$_2$SO$_4$, and evaporated in vacuum. The residue was chromatographed on silica gel using hexane/ethyl acetate (1:2) as an eluent to afford 5.89 g (66%) of cyclobutyl (S)-2-((S)-(((2R,3R,4R,5R)-3-(tert-butoxycarbonyloxy)-5-(2,4-dioxo-3,4-dihydropyrimidin-1(2H)-yl)-4-methyl-4-fluoro-tetrahydrofuran-2-yl)

methoxy)(phenoxy)phosphorylamino)propanoate (8.1) looking like a colorless solidified foam. LC-MS (ESI) 642 (M+H)$^+$.

Similarly, cyclobutyl (S)-2-((((2R,3R,4R,5R)-3-(tert-butoxycarbonyloxy)-5-(2,4-dioxo-3,4-dihydropyrimidin-1(2H)-yl)-4-methyl-4-fluoro-tetrahydrofuran-2-yl)methoxy)(phenoxy)phosphorylamino)propanoate (8) was prepared starting from intermediates 7 and 2 (yield: 52%, LC-MS (ESI) 642 (M+H)$^+$) and cyclobutyl (S)-2-((R)-(((2R,3R,4R,5R)-3-(tert-butoxycarbonyloxy)-5-(2,4-dioxo-3,4-dihydropyrimidin-1(2H)-yl)-4-methyl-4-fluoro-tetrahydrofuran-2-yl)methoxy)(phenoxy)phosphorylamino)propanoate (8.2), starting from intermediates 7 and 2.2 (yield: 59%, LC-MS (ESI) 642 (M+H)$^+$).

To a solution of the compound of formula 8.1 (4.45 g, 6.9 mmol) in dichloromethane (60 ml), trifluoroacetic acid (60 ml) was added at 0° C. The mixture was stirred for 15 h at room temperature, evaporated in vacuum, dissolved in 250 ml of DCM, washed with 300 ml of 5% NaHCO$_3$, dried over Na$_2$SO$_4$, evaporated in vacuum, and recrystallized from a mixture of ethyl acetate and methyl-tert-butyl ether (1:1) to afford 2.7 g (71%) of cyclobutyl (S)-2-((S)-(((2R,3R,4R,5R)-5-(2,4-dioxo-3,4-dihydropyrimidin-1(2H)-yl)-3-hydroxy-4-methyl-4-fluoro-tetrahydrofuran-2-yl)methoxy)-(phenoxy)-phosphorylamino)propanoate (1.1) as a white crystalline substance. LC-MS (ESI) 542 (M+H)$^+$. $^1$H NMR (400 MHz, DMSO-d$_6$) δ 11.51 (brs, 1H), 7.56 (d, J=8.0 Hz, 1H), 7.38 (m, 2H), 7.23 (m, 2H), 7.19 (m, 1H), 6.03 (m, 2H), 5.84 (d, J=6.8 Hz, 1H), 5.55 (dd, J$_1$=8.0 Hz, J$_2$=1.2 Hz, 1H), 4.85 (p, J=7.2 Hz, 1H), 4.37 (m, 1H), 4.27 (m, 1H), 4.01 (m, 1H), 3.83 (m, 2H), 2.23 (m, 2H), 1.95 (m, 2H), 1.71 (m, 1H), 1.56 (m, 1H), 1.25 (d, J=22.8 Hz, 3H), 1.23 (d, J=6.8 Hz, 3H).

Recrystallization of the prodrug of formula 1.1 from various solvents leads to polycrystalline or crystalline forms. Thus, recrystallization from a mixture of ethyl acetate with methyl-tert-butyl ether (1:1), ethanol, ethyl acetate, and a mixture of acetic acid with water yields prodrug 1.1 in polycrystalline forms essentially comprising an orthorhombic phase with unit cell parameters of a=28.1056(8)A, b=16.8998(4)A, and c=5.25380(12)A and a monoclinic phase with unit cell parameters of a=16.2770(6)A, b=16.9117(8)A, c=5.20429(15)A, and β=117.822(2)°.

Recrystallization of the prodrug of formula 1.1 from a mixture of dimethyl sulfoxide with water leands to a white crystalline substance consisting of an orthorhombic phase with unit cell parameters of a=28.1056(8)A, b=16.8998(4) A, and c=5.25380(12)A.

Crystalline and polycrystalline forms have similar solubility values after recrystallization from various solvents at pH 2 and pH7 varying from 0.18 to 0.25 mg/ml. The exception is a polycrystalline sample obtained from recrystallization from dimethyl sulfoxide, the solubility of which is a little higher and varies from 0.63 to 0.67 mg/ml (Table 1).

TABLE 1

Kinetic solubility of polycrystalline and crystalline forms of the prodrug of formula 1.1 for a wavelength of 260 nm

| Prodrug 1.1 recrystallized from | Form of prodrug 1.1 | Solubility, mg/ml | | | |
|---|---|---|---|---|---|
| | | at pH 2 | | at pH 7 | |
| | | value | SD | value | SD |
| A mixture of ethyl acetate and methyl-tert-butyl ether | polycrystal | 0.25 | 0.00 | 0.24 | 0.001 |

TABLE 1-continued

Kinetic solubility of polycrystalline and crystalline forms of the prodrug of formula 1.1 for a wavelength of 260 nm

| Prodrug 1.1 recrystallized from | Form of prodrug 1.1 | Solubility, mg/ml | | | |
|---|---|---|---|---|---|
| | | at pH 2 | | at pH 7 | |
| | | value | SD | value | SD |
| Ethanol | polycrystal | 0.20 | 0.00 | 0.20 | 0.003 |
| Ethyl acetate | polycrystal | 0.22 | 0.00 | 0.22 | 0.002 |
| Acetic acid | polycrystal | 0.63 | 0.009 | 0.67 | 0.041 |
| Dimethyl sulfoxide | crystal | 0.18 | 0.00 | 0.18 | 0.003 |

Similarly, cyclobutyl (S)-2-((((2R,3R,4R,5R)-5-(2,4-dioxo-3,4-dihydropyrimidin-1(2H)-yl)-3-hydroxy-4-methyl-4-fluoro-tetrahydrofuran-2-yl)methoxy)-(phenoxy)-phosphorylamino)propanoate (1) (yield: 58%; LC-MS (ESI) 542 (M+H)$^+$ and cyclobutyl (S)-2-((R)-(((2R,3R,4R,5R)-5-(2,4-dioxo-3,4-dihydropyrimidin-1(2H)-yl)-3-hydroxy-4-methyl-4-fluoro-tetrahydrofuran-2-yl)methoxy)-(phenoxy)-phosphorylamino)propanoate (1.2) (yield: 64%; LC-MS (ESI) 542 (M+H)$^+$. $^1$H ЯМР (300 МГц, ДМСО-d$_6$) δ 11.53 (brs, 1H), 7.56 (d, J=8.1 Hz, 1H), 7.38 (m, 2H), 7.19 (m, 3H), 6.08 (m, 2H), 5.91 (d, J=6.3 Hz, 1H), 5.57 (d, J=8.1 Hz, 1H), 4.85 (p, J=7.5 Hz, 1H), 4.41 (m, 1H), 4.27 (m, 1H), 4.05 (m, 1H), 3.79 (m, 2H), 2.23 (m, 2H), 1.94 (m, 2H), 1.70 (m, 1H), 1.56 (m, 1H), 1.24 (d, J=23.4 Hz, 3H), 1.21 (d, J=6.0 Hz, 3H) were prepared.

Example 2. Synthetic Protocol for the Prodrug of Cyclopropyl (S)-2-((S)-(((2R,3R,4R,5R)-5-(2,4-dioxo-3,4-dihydropyrimidin-1(2H)-yl)-3-hydroxy-4-methyl-4-fluoro-tetrahydrofuran-2-yl)methoxy)-(phenoxy)-phosphorylamino)propanoate of Formula A2 (Scheme 2)

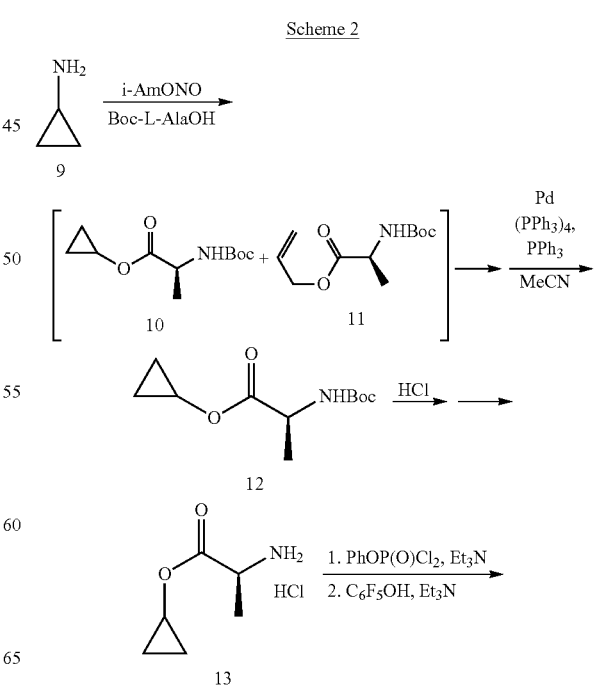

-continued

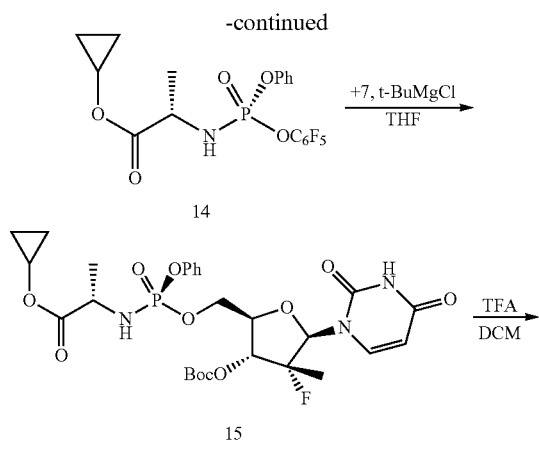

Cyclopropylamine (9: 4.06 ml, 58.8 mmol) and Boc-L-alanine (22.2 g, 58.8 mmol) were dissolved in 250 ml of chloroform, and isoamyl nitrite (7.9 ml, 58.8 mmol) was added under cooling with ice. The mixture was stirred under cooling for 16 h, evaporated till dry, and chromatographed on silica gel (eluting with ethyl acetate:hexane 1:8) to afford 7.68 g (57%) of a mixture of cyclopropyl ester of formula 10 and allyl ether of formula 11 in a ratio of 1:4 (based on $^1$H NMR data). The resulting mixture of ester 10 and ether 11 was dissolved in 120 ml of acetonitrile, whereupon triphenylphosphine (446 mg, 1.7 mmol) and Pd(PPh$_3$)$_4$ (984 mg, 0.85 mmol) were added under argon. The solution was cooled with ice and diluted with a solution of pyrrolidine (2.49 g, 35 mmol) in acetonitrile (30 ml). The mixture was stirred 16 h under argon at 0-4° C., evaporated till dry, and chromatographed on silica gel (eluting with ethyl acetate:hexane 1:8) to afford 1.38 g of (S)-cyclopropyl 2-(tert-butoxycarbonylamino)propanoate (15). $^1$H NMR (CDCl$_3$, 400 MHz) δ 5.04 (br.s., 1H), 4.26 (m, 1H), 4.19 (m, 1H), 1.46 (c, 9H), 1.37 (d, J=7.2 Hz, 3H), 0.74 (m, 4H).

To a solution of the compound of formula 12 (3.5 g, 15.3 mmol) in 10 ml of dioxane, 20 ml of a 3M HCl solution in dioxane was added. The mixture was stirred 2 h at room temperature and evaporated till dry to afford 2.53 g of (S)-cyclopropyl 2-amino-propanoate hydrochloride (13). $^1$H NMR (DMSO-d$_6$, 300 MHz) δ 8.65 (br.s., 3H), 4.19 (m, 1H), 3.99 (к, J=6.9 Hz, 1H), 1.39 (d, J=6.9 Hz, 3H), 0.73 (m, 4H).

To a solution of the compound of formula 13 ((2.53 g, 15.3 mmol) and phenyldichlorophosphate (3.23 g, 15.3 mmol) in 50 ml of dichloromethane cooled down to −70° C., a solution of triethylamine (4.26 ml, 30.6 mmol) in 10 ml of dichloromethane was added dropwise. The temperature of the reaction mixture was then allowed to rise to −10° C., and a mixture of pentafluorophenol (2.82 g, 15.3 mmol) and triethylamine (2.13 ml, 15.3 mmol) in 15 ml of dichloromethane, which had been prepared beforehand, was added dropwise. Upon completion of addition, the reaction mixture was stirred for 12 h at room temperature, then evaporated, and the residue was treated with 50 ml of benzene. The residue was filtered off and washed with 15 ml of benzene. The filtrate was washed with a saturated sodium hydrocarbonate solution, dried over sodium sulfate, and evaporated. A mixture of ethyl acetate:hexane 1:4 at a rate of 8 ml per 1 g of the substance was added to the residue, and the resulting mixture was vigorously stirred for 16 h. The residue was filtered off and recrystallized from a mixture of ethyl acetate:hexane 1:4 to afford 1.02 g (14%) of (S)-cyclopropyl 2-((S)-(perfluorophenoxy)-phosphorylamino) propanoate (14). LC-MS (ESI) 452 (M+H)$^+$. $^1$H NMR (CDCl$_3$, 300 MHz) δ 7.38 (m, 2H), 7.26 (m, 3H), 4.7 (m, 1H), 3.96 (m, 1H), 1.46 (d, J=7.2 Hz, 3H), 0.74 (m, 4H).

To a solution of tert-butyl (2R,3R,4R,5R)-5-(2,4-dioxo-3,4-dihydropyrimidin-1(2H)-yl)-2-(hydroxymethyl)-4-methyl-4-fluoro-tetrahydrofuran-3-yl carbonate (820 mg, 1.85 mmol) in 25 ml of dry THF cooled with ice, a 1M solution of t-BuMgCl in THF (4 ml, 0.4 mmol) was added dropwise. The cooling was terminated and the reaction mixture was stirred 0.5 h at room temperature, then cooled with ice again, and a solution of the compound of formula 14 (1.02 g, 2.18 mmol) in THF was added dropwise. The reaction mixture was stirred for 12 h at room temperature and then treated with a saturated ammonium chloride solution. The organic phase was separated, and the aqueous phase was extracted with dichloromethane. The combined extracts were dried over sodium sulfate and filtered to afford ~1.16 g of (S)-cyclopropyl 2-((S)-(((2R,3R,4R,5R)-3-(tert-butoxycarbonyloxy)-5-(2,4-dioxo-3,4-dihydropyrimidin-1(2H)-yl)-4-methyl-4-fluoro-tetrahydrofuran-2-yl)methoxy)-(phenoxy)-phosphorylamino)propanoate (15), which was used at the next stage as such. LC-MS (ESI) 628 (M+H)$^+$.

To a solution of the compound of formula 15 (~1.16 g, 1.85 mmol) in 20 ml of dichloromethane, trifluoroacetic acid (20 ml) was added under cooling with ice. The reaction mixture was stirred for 3 h and then concentrated in vacuo. The residue was dissolved in dichloromethane, diluted with water, and neutralized with sodium hydrocarbonate. The organic layer was separated, dried over sodium sulfate, and evaporated till dry. The residue was chromatographed on silica gel (chloroform:methanol) and recrystallized from a mixture of ethyl acetate:MTBE to afford 505 mg of (S)-cyclopropyl 2-((S)-(((2R,3R,4R,5R)-5-(2,4-dioxo-3,4-dihydropyrimidin-1(2H)-yl)-3-hydroxy-4-methyl-4-fluoro-tetrahydrofuran-2-yl)methoxy)-(phenoxy)-phosphorylamino) propanoate of formula A2 (52%). LC-MS (ESI) 528 (M+H)$^+$. $^1$H NMR (DMSO-d$_6$, 400 MHz) δ 11.24 (br. s., 1H), 7.56 (d, J=8.1 Hz, 1H), 7.38 (m, 2H), 7.20 (m, 3H), 6.05 (m, 2H), 5.86 (m, 1H), 5.54 (d, J=8.1 Hz, 1H), 4.36 (m, 1H), 4.23 (m, 1H), 4.02 (m, 2H), 3.82 (m, 2H), 1.25 (d, J=22.2 Hz, 3H), 1.21 (d, J=6.6 Hz, 3H), 0.66 (m, 2H), 0.57 (m, 2H).

Example 3. Preparation of a Pharmaceutical Composition in the Form of Tablet

Starch (500 mg), ground lactose (800 mg), talc (200 mg), and 1500 mg of the prodrug of formula 1.1 were mixed together and pressed into bar. The resulting bar was comminuted into granules and sifted through a sieve to collect granules of 14-16 mesh. The granules thus obtained were shaped into tablets of suitable form weighing 400 or 800 mg each.

Example 4. Preparation of a Pharmaceutical Composition in the Form of Capsules

The prodrug of formula 1.1 was carefully mixed with a lactose powder in a ratio of 1:1. The resulting powdery mixture was packed into gelatin capsules of suitable size with either 200 or 400 mg in each capsule.

Example 5. Preparation of a Pharmaceutical Composition in the Form of Compositions for Intramuscular, Intraperitoneal, or Subcutaneous Injections The prodrug of formula 1.1 (500 mg) was mixed with chlorobutanol (300 ml), propylene glycol (2 ml), and injectable water. The resulting solution was filtered, placed into 5 ml ampoules, and sealed.

Example 6. Evaluation of Anti-HCV Activity and Cytotoxicity for the Prodrugs of Formulas 1.1 and A2 and Sovaldi®

The antiviral activity of tested compositions comprising the prodrugs was evaluated using an Huh7 human hepatocellular carcinoma cell line stably transfected with an HCV replicon. A cell suspension in a complete culture medium (DMEM 1×, Cellgro; cat. #10-013-CV) was transferred into 96-well plates (50 µl per well) with a final density of 7500 cells per well. The serial dilutions of tested prodrugs were prepared from a fresh 200-fold generic solution in DMSO with 11 concentration points and 3-fold increments starting from 20 nM in a complete medium and were used in two replicates. Minimum 4 hours after planting the cells, 50 µl of serial prodrug dilutions was added to each well. The final prodrug concentration varied from 10 nM to 0.1 pM and that of DMSO, 0.5%. The plate with cells was incubated for 3 days at 37° C. under humidified 5% $CO_2$. Upon completion of incubation, the medium was removed by turning the plate over and shaking it carefully. The cells were fixed for one minute with 100 µl of a 1: acetone:methanol solution, washed 3 times with a phosphate buffer (PBS), and blocked for 1 h at room temperature using a 10% fetal bovine serum (FBS) in PBS (150 µl/well). The cells were washed 3 times with PBS and incubated for 2 h at 37° C. with anti-NS5B HCV antibodies (100 µl/well) using Affinity BioReagents (cat. # MA1-080) and diluting the generic solution (1 mg/ml) in a ratio of 1:4000 in 10% FBS-PBS. The cells were washed 3 times with PBS and developed by an OPD solution (100 µl/well) using for each plate one OPD tablet dissolved in a citrate/phosphate buffer (12 ml), whereto 5 µl of 30% $H_2O_2$ was added, for 30 minutes in the dark at room temperature. The reaction was stopped by 2N $H_2SO_4$ (100 µl/well), and OD490 was measured using the multifunctional reader Victor³ V 1420 (Perkin Elmer). The values of $EC_{50}$ for tested prodrugs were measured from an activity curve plotted using the GraphPad Prizm software. The novel prodrug of formula 1.1 has against the 1b (gT1b) HCV genotype $EC_{50}$=15.0-27.0 nM and $EC_{90}$=128.0 nM; Sovaldi®, $EC_{50}$=45-170 nM and $EC_{90}$=590 nM; the cyclohexyl ester of formula A1, $EC_{90}$=250.0 nM; and the cyclopropyl ester of formula A2, $EC_{90}$=73.0 nM and $EC_{90}$=410.0 nM (Table 1a). Consequently, the activity of the novel prodrug of formula 1.1 more than three times exceeds that of Sovaldi®, two times that of the compound of formula A1, and more than three times that of the compound of formula A2.

TABLE 1a

Inhibiting activity of the prodrugs of formulas 1.1, A1, and A2 and Sovaldi ® against gT1b HCV NS5B

| | 10% FBS | | |
|---|---|---|---|
| Prodrug | $EC_{50}$, nM | $EC_{90}$, nM | $CC_{90}$, µM |
| 1.1 | 15.0-27.0 | 128.0 | >100 |
| *Sovaldi ® | 45.0-170.0* | 520.0** | >100** |
| A1 | | 250.0** | |
| A2 | 73.0 | 410.0 | |

From:
*http//www.hcvdruginfo.ca/HCV_Sofosbuvir.pdf;
**M. J. Sofia et al. *J. Med. Chem.* 2010, 53, 7202-7218.

The cytotoxicity of tested compositions comprising the prodrugs was evaluated concurrently in the same cell line Huh7 using an ATPLite kit (Perkin-Elmer, Boston, USA) in accordance with the manufacturer's instruction. The cell suspension in complete culture medium (DMEM 1×, Cellgro; cat. #10-013-CV) was transferred into 96-well plates with black walls and transparent bottoms (50 µl/well) with a final density of 7500 cells per well. Eighteen hours after planting the cells, serial drug dilutions (50 µl/well) were added. The plate with cells was incubated for 4 days at 37° C. in a humidified 5% $CO_2$ atmosphere. The cells were then twice washed with PBS (200 µl/well) and lysed by adding a lytic buffer (50 µl/well); all reagents were taken from the ATPLite kit. Following a 5-minute stirring on a shaker, a substrate was added (50 µl/well). After an additional 5-minute incubation, the plate was kept for 10 minutes in the dark, and luminescence in the wells was measured using the multifunctional reader Victor³ V 1420 (Perkin Elmer). The values of $CC_{50}$ for tested prodrugs were measured from a cytotoxicity curve plotted using the GraphPad Prizm software. In particular, for the novel prodrug of formula 1.1 cytotoxicity was found to be $CC_{50}$>100 µM (Table 1a) and the therapeutic window (therapeutic index TI=$EC_{50}$/$CC_{50}$), TI>6 000.0.

Example 7. Evaluation of Kinetic Solubility for Compounds

Principle of the Method.

The tested compound was dissolved in DMSO to reach a 10-mM concentration and then poured into an aqueous solvent (a phosphate buffer, water, or universal buffers of different pH values) to bring the concentration down to 200 µM. The resulting solution placed in a 96-well filter plate (Millipore's MultiScreen Solubility Filter Plate) was incubated for an hour at room temperature on a shaker, and the residue was filtered off in vacuo. The absorption spectrum of the compound was recorded on a spectrophotometer in a range of 240-400 nm with a 10-nm increment. For quantitative estimation of solubility, a calibration curve of standard solutions (0-200 µM) comprising 40% acetonitrile was used. The range of estimated concentrations was 3-200 µM. The test procedure was performed in duplicates.

Preparation of Calibration Standards.

Calibration standards were prepared from 50-fold stock solutions in DMSO diluted in a buffer with 40% acetonitrile, which was added to ensure complete solubility of the tested compound in the calibration sample. Six standard samples with concentrations of 0, 3.125, 12.5, 50, 100, and 200 µM were prepared in the wells of a UV 96-well plate by adding 4 µl of corresponding 50× stock solutions in DMSO to 196

µl of a buffer comprising 40% acetonitrile. The concentration of DMSO in all points was constant and equal to 2% (v/v).

To plot calibration curves, the optical spectrum of the UV plate was recorded in a wavelength range of 250-400 nm with a 10-nm increment. Based on the spectral data for each compound, wavelengths were selected to meet the following criteria:

For minimum compound concentration, OD>0.1 (AU);
For maximum compound concentration, OD<2.0.

For each compound, a calibration curve was plotted with OD at selected wavelength as a function of concentration.

Evaluation of Kinetic Solubility for Compounds.

Solubility was evaluated in a MultiScreen Solubility (Millipore Corp.) filter plate as follows:

Into each well of the MultiScreen Solubility filter plate, 196 µl of a buffer (without acetonitrile) and 4 µl of a 10-mM compound in DMSO or 4 µl of DMSO (for a blank matrix) were added. The plate was incubated for one hour on a shaker (400 rpm) at room temperature.

The resulting solutions were filtered off through the filter plate by means of vacuum (10″ Hg) into a polypropylene plate with a U-shaped bottom.

From the U-bottom plate, the filtrate (120 µl/well) was transferred into a new UV plate, whereto acetonitrile (80 µl/well) was added.

The optical density of resulting solutionов for a preselected wavelength was measured for each compound.

Calculations.

The final compound concentration in the filtrate was computed as follows:

$$C_{filtrate}=(OD_\lambda Filtrate-OD_\lambda Blank)/Slope \times 1.67,$$

wherein:

$OD_\lambda$ Filtrate is the optical density of filtrate for a selected wavelength;

$OD_\lambda$ Blank is OD of a blank matrix;

Slope is the gradient of the calibration line;

1.67 is dilution factor for the filtrate diluted with acetonitrile.

The findings are presented in Table 1.

Example 8. X-Ray Powder Phase Analysis of Prodrug Samples

All diffraction patterns were recorded on a Bruker D8 Advance Vario diffractometer equipped with a copper-anode X-ray tube and a Ge(111) monochromator (CuKoˆ) and a LynxEye position-sensitive detector, in peek-a-boo settings. The shot range was 3-90° 2θ for sample s5 and 5.7-90° 2θ for the other samples, and the increment was 0.01° 2θ. The analysis was carried out using the Bruker Topas5 software ['Bruker TOPAS 5 User Manual.—Karlsruhe, Germany: Bruker AXS GmbH, 2015.].

Samples obtained by recrystallization of the compound of formula 1.1 from a mixture of ethyl acetate and methyl-tert-butyl ether (1:1), ethanol, ethyl acetate, and a mixture of acetic acid with water had polycrystalline forms. X-ray powder phase analyses of these samples revealed a similarity of their qualitative phase structures and an insignificant difference in their phase relations. The samples had an orthorhombic phase with the following unit cell parameters: a=28.1056(8) A, b=16.8998(4) A, and c=5.25380(12) A. Systematic extinction analysis allows one to assume a spatial group of $P2_12_12_1$. A unit cell volume of 2495.45(11) $A^3$ corresponds to the claimed composition and Z'=1. The samples also have a monoclinic phase with the following unit cell parameters: a=16.2770(6) A, b=16.9117(8) A, c=5.20429(15) A, β=117.822(2°). Systematic extinction analysis allows one to assume a spatial group of $P2_1$. A unit cell volume of 1266.98(9) $A^3$ corresponds to the claimed composition and Z'=1. The evaluation of phase relations based on comparisons of integral peak intensities suggests that the content of monoclinic phase varies from 30 to 50%.

The sample obtained by recrystallization of the compound of formula 1.1 from a mixture of dimethyl sulfoxide with water is a white substance of crystalline form. According to X-ray powder analysis data, the sample of said form is single-phase and consists of an orthorhombic phase with the following unit cell parameters: a=28.1056(8) A, b=16.8998 (4) A, c=5.25380(12) A. Systematic extinction analysis allows one to assume a spatial group of $P2_12_12_1$. A unit cell volume of 2495.45(11) $A^3$ corresponds to the claimed composition and Z'=1.

Example 9. Evaluation of Stability in Biological Matrix for Compositions Comprising the Prodrug of Formula 1.1

Initial compositions comprising the prodrug of formula 1.1 (the tested compound) were prepared in a concentration of 10 mM in DMSO. From said compositions, 100-fold working solutions were prepared in a concentration of 100 µM in a mixture of acetonitrile:water at a ratio of 1:1 by volume.

a) Stability in S9 Fraction.

The reaction mixture was prepared in a 0.1 M potassium phosphate buffer (pH 7.4 BD Gentest) in a total final volume of 250 µl and contained a 1 mM NADPH-tetrasodium salt (AppliChem), 7 mM glucose-6-phosphate sodium salt (Sigma), 1.5 U/ml glucose-6-phosphate dehydrogenase (Sigma), 3.3 mM $MgCl_2$ (Sigma), 5 mM uridine-5-diphosphate-glucuronic acid trisodium salt (UDPGluA, Sigma), and 1 µM tested compound (these are final concentrations). The metabolic reaction was initiated by adding a suspension of human liver S9 fraction (BD Gentest), and the final concentration of protein was 1 mg/ml. The reaction mixture was incubated at 37° C. on a Vortemp56 shaker with stirring at 400 rpm. After certain intervals (0, 0.25, 0.5, 1, 2, 4, 6, 8, 24 h), 30-µl samples were taken; the reaction was stopped by adding cold acetonitrile (180 µl) comprising the internal standard to the sample taken. Proteins were deposited on ice for 15 min. The samples were then centrifuged for 10 min at 3000 rpm, and the supernatant (150 µl) was sampled for analysis. The incubation was performed in two replicates, with each sample measured twice.

b) Stability in Artificial Gastric and Intestinal Juices.

The tested composition comprising the prodrug of formula 1.1 in a final concentration of 1 µM was incubated in artificial gastric juice (0.2% NaCl in 0.7% v/v HCl) and artificial intestinal juice (0.05M $KH_2PO_4$, pH 6.75). The incubation was performed in a Vortemp56 shaking incubator at 37° C. with stirring at a rate of 300 rev/min. After certain intervals (0, 0.25, 0.5, 1, 2, 4, 6, 8, 24 h), a 30 µl sample was taken; the reaction was stopped by adding cold acetonitrile (180 µl) comprising the internal standard to the sample taken. The samples were then centrifuged, and the supernatant (150 µl) was sampled for analysis for 10 min at 3000 rev/min. The incubation was performed in two replicates, with each sample measured twice.

c) Stability in Blood Plasma.

The tested compound in a final concentration of 1 µM was incubated in pooled human blood plasma (Innovative Research). The incubation was performed in a Vortemp56 shaking incubator at 37° C. with stirring at a rate of 300 rev/min. After certain intervals (0, 0.25, 0.5, 1, 2, 4, 6, 8, 24 h), a 30 μl sample was taken; the reaction was stopped by adding cold acetonitrile (180 μl) comprising the internal standard to the sample taken. The samples were then centrifuged, and the supernatant (150 μl) was sampled for analysis for 10 min at 3000 rev/min. The incubation was performed in two replicates, with each sample measured twice.

Sample Analysis.

Samples were analyzed using an HPLC-MS/MS technique developed for each tested prodrug, wherein the chromatographic system 1290 Infinity II (Agilent Technologies) was combined with the tandem mass spectrometer QTRAP5500 (AB Sciex). When developing conditions for mass-spectrometric detection, the solutions of tested compounds in a mixture of acetonitrile-water (1:1) in a concentration of 100 ng/ml were injected directly into the mass spectrometer using a syringe pump with electrospray ionization carried out in a positive ion mode. Scanning in a total ion current mode (MS1) allowed us to identify a molecular ion for each compound, and basic product ions were recorded in MS2 mode. Then, to attain maximum sensitivity, the MS/MS technique was optimized in MRM mode. In quantitative chromatogram processing, the most intensive MRM transition was used for the analyte and the internal standard. Separation was carried out by means of linear gradient elution chromatography on a YMC Triart C18 column (50×2 mm, 1.9 μm) in a mobile phase consisting of 0.1% formic acid in water and 0.1% formic acid in acetonitrile. Tolbutamide (Fluka) was used as the internal standard.

Computations.

Half-life ($T_{1/2}$) was found from the kinetics of tested prodrug elimination in an antiviral composition during incubation in a biological matrix. The computations were based on the values of chromatographic peak areas for compounds in test samples normalized to the internal standard signal. From linear dependence of log normalized areas of chromatographic peaks on time, the constant of elimination rate was calculated (k is linear section slope). Then, half-life was found: $T_{1/2}=0.693/k$. It was discovered, in particular (Table 2), that the prodrug of formula 1.1, the compound of formula A1, and Sovaldi® had comparable stabilities in human gastric juice ($T_{1/2}^{SGF}=12.7$-17 h), in human intestinal juice ($T_{1/2}^{SIF}>20$ h), and in human plasma ($T_{1/2}^{HPL}>24$ h). At the same time, the prodrug of formula 1.1 more actively metabolized in human liver microsomal S9 fraction and has half-life $T_{1/2}^{HS9}=0.05$ h, while its prototype Sovaldi® has $T_{1/2}^{HS9}=0.57$ h and cyclohexyl ester of formula A1, $T_{1/2}^{HS9}=1.4$ h (Table 2), which means that the prodrug of formula 1.1 metabolizes in human liver microsomal S9 fraction 11 times faster than Sovaldi® and 28 times faster than the compound of formula A1.

TABLE 2

Stability and activity of antiviral compositions comprising the novel prodrug of formula 1.1 and Sovaldi ®

| | $T_{1/2}$ (h) | | | |
|---|---|---|---|---|
| ID | SGF | SIF | human plasma | human S9 |
| 1.1 | 12.7 | >24 | >24 | 0.05 |
| Sovaldi ® | 22.0* | >24* | >24* | 0.57* |
| A1 | 17* | >20* | >24* | 1.4* |

*from M. J. Sofia et al. *J. Med. Chem.* 2010, 53, 7202-7218.

Example 10. Pharmacokinetic (PK) Study of Compositions Comprising the Prodrug of Formula 1.1 and Sovaldi® in Rat Liver Preparation of Compositions Comprising the Prodrug of Formula 1.1 and Sovaldi® for Administration to Rats.

The tested composition was administered at a dose of 50 mg/kg. To this end, compositions were prepared in a concentration of the prodrug of formula 1.1 or Sovaldi® of 5.0 mg/ml in a 0.5% solution of hydroxypropyl methylcellulose (HPMC), to which 5% ethanol was added, as follows: to a weighed portion of the prodrug of formula 1.1 or Sovaldi®, an appropriate amount of HPMC was added, and the mixture was triturated dry in a mortar, whereafter a proper quantity of 5% ethanol in distilled water was gradually added portionwise, and the mixture was carefully stirred to obtain a suspension suitable for intragastric administration.

Administration of Compositions Comprising the Prodrug of Formula 1.1 and Sovaldi® to Animals.

Preparation of blood plasma and liver samples. The study was carried out on Sprague Dawley rats. The rats were divided into groups of 6 based on selected time points (1, 2, 4, 6, 8, 10, 12, 16, and 24 h). The rats were weighed, and the volume of compositions comprising the prodrug of formula 1.1 or Sovaldi® were administered intragastrically through a feeding tube. In the intervals between administrations to the animals of a certain group, samples of liver and blood were taken. After an appropriate period of time following the administration, the rat was euthanized by $CO_2$ inhalation. Immediately after the euthanasia, the animal was quickly opened up, and its upper lobe of the liver was cut and instantaneously placed in liquid nitrogen. The frozen liver fragment was then transferred into a labeled test tube cooled with liquid nitrogen. The samples were kept in liquid nitrogen till the end of the experiment and then put into an ultra-cold freezer at −80° C.

Sample Preparation.

A liver sample weighing about 1 g was triturated in a mortar while being cooled with liquid nitrogen. The resulting powder was poured over with triple-volume methanol and 70% methanol with EDTA and twice homogenized for 45 s (with a 10-second interval) at a rate of 6.3 m/s using the Omni Bead Ruptor 24 homogenizer. To 360 μl of thus obtained homogenate, 40 μl of ten-fold standard solution comprising PSI-7409 and H027-4261 (or methanol, in case of experimental samples) and 100 μl of internal standard solution (5-bromouridine triphosphate) in a concentration of 25 ng/ml were added. After stirring and centrifuging, 400 μl of supernatant was diluted with 400 μl of a 1% formic acid solution in a mixture of methanol-water (1:1). Then, solid-phase extraction was performed using Waters Oasis WAX cartridges. The resulting product was eluted with 800 μl of a 5% solution of ammonia in methanol, and the eluate was evaporated and redissolved in 200 μl of methanol.

HPLC-MS/MS Analytical Conditions.

Samples were analyzed using an HPLC-MS/MS technique, wherein the HPLC system Agilent 1290 Infinity II was combined with the AB Sciex QTrap 5500 mass spectrometer. Separation was carried out on a Thermo Hypercarb column (50×3 mm, 5 μm). A 25-mM solution of ammonium acetate with 0.5% ammonium was used as mobile phase A (MPA); a 25-mM solution of ammonium acetate in a mixture of water-isopropanol-acetonitrile (1:1:3) with 0.5% ammonium was used as mobile phase B (MPB). Separation was performed in gradient mode: 0-0.3 min-5% MPB; 3-3.4 min-50% MPB; 3.6-4.5 min-5% MPB. PSI-7409 and H027-

4261 were recorded in MRM mode with ion transitions of 499/159 and 410/150, respectively.

Pharmacokinetic Analysis.

Pharmacokinetic analysis of "liver concentration versus time" data was performed by a non-compartmental technique using Phoenix™ WinNonlin® 6.3 (Pharsight Corp.) and GraphPad Prizm software. The following pharmacokinetic parameters were computed: maximum concentration in liver ($C_{max}$) and time of achievement thereof ($T_{max}$), half-life ($T_{1/2}$), and area under the PK curve ($AUC_{0-t}$, $AUC_{0-inf}$). The findings are given in Table 3. As can be seen from Table 3, the concentration and $AUC_{24h}$ of triphosphate PSI-7409 resulting from the metabolism of the prodrug of formula 1.1 in rat liver are $C_{max}$=3224.0 ng/g and $AUC_{24\ h}$=30487.0 ng·h/g, respectively, while Sovaldi® exhibiting similar metabolism has $C_{max}$=1934.0 ng/g and $AUC_{24\ h}$=16796.0 ng·h/g, and cyclohexyl ester of formula A1 has $C_{max}$=557 ng/g and $AUC_{24\ h}$=6484.0 ng h/g (Table 3). This suggests that the novel prodrug of formula 1.1 is almost twice more effective in its liver metabolism into desired triphosphate PSI-7409 (drug) as compared to Sovaldi® and 4.7 times, as compared to cyclohexyl ester of formula A1.

TABLE 3

Pharmacokinetic (PK) parameters of triphosphate PSI-7409 in rat liver following peroral administration of the prodrug of formula 1.1 and Sovaldi ® in a dose of 50 mg/kg

| | Software used for processing PK results | | According to M. J. Sofia et al. *J. Med. Chem.* 2010, 53, 7202-7218. | |
| --- | --- | --- | --- | --- |
| | Phoenix ™ WinNonlin ® 6.3 | GraphPad Prizm | | |
| PK parameters | Prodrug 1.1 | | Sovaldi ® | Prodrug A1 |
| $T_{1/2}$, h | 7.2 | 5.5 | | |
| $T_{max}$, h | 8.0 | 4.0 | 4.0 | 2.0 |
| $C_{max}$, ng/g | 3224.0 | 3102.0 | 1934 | 557.0 |
| $C_{24\ h}$, ng/g | 320.0 | | | |
| $AUC_{24\ h}$, ng · h/g | 30487.0 | 30444.0 | 16796.0 | 6487.0 |
| $AUC_{0-inf}$, ng · h/g | 33823.0 | | 18080.0 | 8831.0 |

INDUSTRIAL APPLICABILITY

The invention could be used in medicine and veterinary.

The invention claimed is:

1. Cyclobutyl (S)-2-{[(2R,3R,4R,5R)-5-(2,4-dioxo-3,4-dihydro-2H-pyrimidin-1-yl)-4-fluoro-3-hydroxy-4-methyl-tetrahydrofuran-2-ylmethoxy]-phenoxy-phosphorylamino}propanoate of general formula 1, its stereoisomer, isotopically enriched analog, crystalline or polycrystalline form,

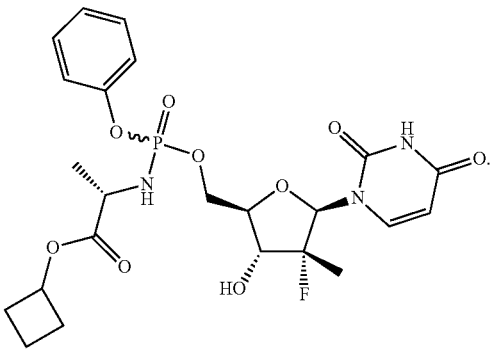

2. The compound according to claim 1, which is cyclobutyl (S)-2-{(S)-[(2R,3R,4R,5R)-5-(3,4-dihydro-2,4-dioxo-2H-pyrimidin-1-yl)-3-hydroxy-4-methyl-4-fluoro-tetrahydrofuran-2-ylmethoxy]-phenoxy-phosphorylamino}propanoate of formula 1.1 or cyclobutyl (S)-2-{(R)-[(2R,3R,4R,5R)-5-(3,4-dihydro-2,4-dioxo-2H-pyrimidin-1-yl)-3-hydroxy-4-methyl-4-fluoro-tetrahydrofuran-2-ylmethoxy]-phenoxy-phosphorylamino}propanoate of formula 1.2, their isotopically enriched analog, crystalline or polycrystalline form,

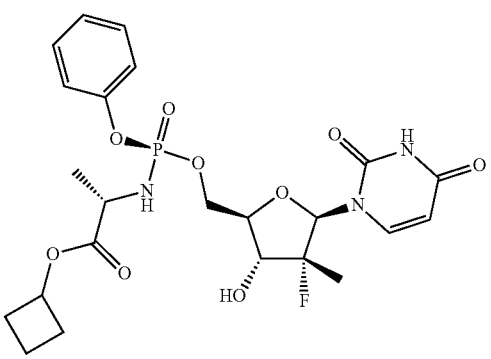

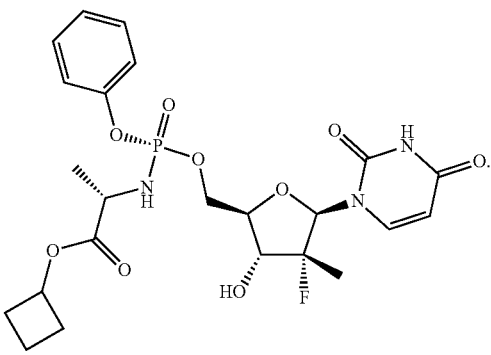

3. A method of inhibiting an HCV NS5B polymerase by contacting said polymerase with a compound of claim 1.

4. A method for the production of the compound as in any one of claims 1 and 2, including the use of cyclobutyl (S)-2-(pentafluorophenyloxy-phenoxy-phosphorylamino) propionate of formula 2, or its stereoisomers: cyclobutyl (S)-2-((S)-pentafluorophenyloxy-phenoxy-phosphorylamino)propionate of formula 2.1 or cyclobutyl (S)-2-((R)-pentafluorophenyloxy-phenoxy-phosphorylamino)propionate of formula 2.2,

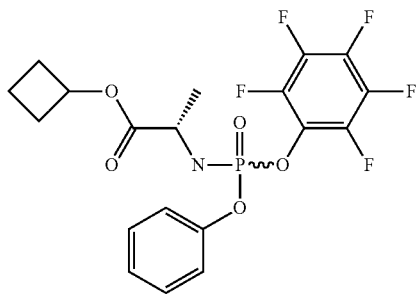

2.1

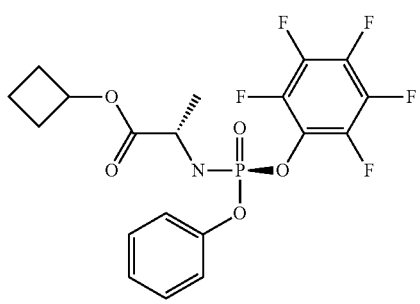

2.2

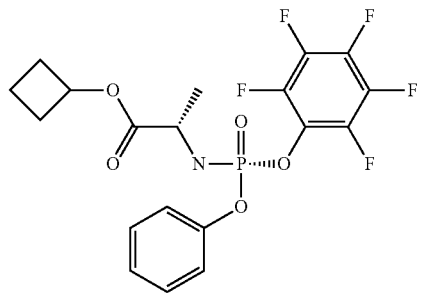

and tert-butyl (2R,3R,4R,5R)-5-(2,4-dioxo-3,4-dihydropyrimidin-1(2H)-yl)-2-(hydroxymethyl)-4-methyl-4-fluoro tetrahydrofuran-3-yl carbonate of formula 7

7

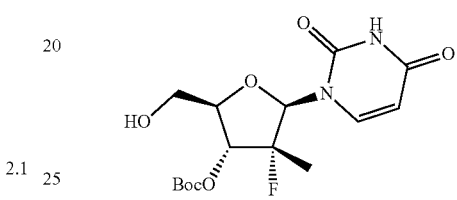

in the presence of alkylmagnesium halogenide, followed by removal of the protective group and obtaining the corresponding compound 1, 1.1 and 1.2 and, if necessary, its crystallization.

5. A pharmaceutical composition comprising the compound of claim 1 in a therapeutically effective amount and a pharmaceutically acceptable carrier.

6. A method for the treatment of a subject infected with hepatitis C virus including the administration to the subject of an effective amount of the pharmaceutical composition of claim 5 or the compound or its stereoisomer according to claim 1 or their isotopically enriched analog, crystalline or polycrystalline form.

* * * * *